US011944828B2

(12) United States Patent
Yang et al.

(10) Patent No.: US 11,944,828 B2
(45) Date of Patent: Apr. 2, 2024

(54) ROTATABLE ADAPTER FOR CONNECTING IMPLANTABLE MEDICAL LEADS TO TEST DEVICES

(71) Applicant: Medtronic, Inc., Minneapolis, MN (US)

(72) Inventors: Zhongping Yang, Woodbury, MN (US); Thomas A. Anderson, New Hope, MN (US); Wade M. Demmer, Coon Rapids, MN (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/348,666

(22) Filed: Jun. 15, 2021

(65) Prior Publication Data

US 2022/0088395 A1    Mar. 24, 2022

Related U.S. Application Data

(60) Provisional application No. 63/082,615, filed on Sep. 24, 2020.

(51) Int. Cl.
*A61N 1/04* (2006.01)
*A61N 1/375* (2006.01)

(52) U.S. Cl.
CPC ....... *A61N 1/3752* (2013.01); *A61N 1/37512* (2017.08)

(58) Field of Classification Search
None
See application file for complete search history.

(56) References Cited

U.S. PATENT DOCUMENTS

| 4,209,019 A | 6/1980 | Dutcher et al. |
| 4,624,266 A | 11/1986 | Kane |
| 4,764,132 A | 8/1988 | Stutz |
| 4,795,370 A | 1/1989 | Freitag |
| 7,035,689 B1 | 4/2006 | Hawkins et al. |

(Continued)

FOREIGN PATENT DOCUMENTS

| CN | 109529195 A | 3/2019 | |
| CN | 111244705 A | * 6/2020 | ............ H01R 11/24 |
| EP | 2676698 A1 | 12/2013 | |

OTHER PUBLICATIONS

International Search Report and Written Opinion of International Application No. PCT/US2021/050228, dated Jan. 5, 2022, 11 pp.

*Primary Examiner* — Erica S Lee

(74) *Attorney, Agent, or Firm* — Shumaker & Sieffert, P.A.

(57) ABSTRACT

An adapter configured to electrically connect a test device to an implantable medical lead comprises a rotational electrical coupling. The rotational electrical coupling is configured to electrically connect a lead electrical connector to an adapter electrical connector. The rotational electrical coupling comprises a first conductive component configured to be electrically connected to the lead electrical connector and rotatable with a proximal portion of the implantable medical lead, and a second conductive component electrically connected to the first conductive component and the adapter electrical connector. The second conductive component may be rotationally fixed. The first and second conductive components may comprise graphite or another soft metal.

19 Claims, 9 Drawing Sheets

(56) References Cited

U.S. PATENT DOCUMENTS

| | | |
|---|---|---|
| 7,753,696 B2 | 7/2010 | Hoecke et al. |
| 8,958,878 B2 | 2/2015 | Cejnar |
| 9,059,548 B2 | 6/2015 | Stump et al. |
| 9,212,981 B2 | 12/2015 | Mercer et al. |
| 9,302,092 B2 | 4/2016 | Ware et al. |
| 10,644,468 B2 * | 5/2020 | White .................... H01R 13/02 |
| 2006/0258193 A1 | 11/2006 | Hoecke et al. |
| 2008/0015668 A1 | 1/2008 | Soukup |
| 2009/0004929 A1 | 1/2009 | Kainz |
| 2009/0276003 A1 | 11/2009 | Sommer et al. |
| 2011/0160824 A1 | 6/2011 | Ware et al. |
| 2012/0071945 A1 | 3/2012 | Cejnar |
| 2015/0165217 A1 * | 6/2015 | Hughes ................ A61N 1/3752 |
| | | 29/842 |
| 2020/0094058 A1 * | 3/2020 | Mangual-Soto ....... A61N 1/371 |
| 2020/0222685 A1 * | 7/2020 | De Kock ............... H01R 31/06 |
| 2022/0336998 A1 | 10/2022 | Jiang |

\* cited by examiner

ROTATABLE ADAPTER FOR CONNECTING IMPLANTABLE MEDICAL LEADS TO TEST DEVICES

This application claims the benefit of U.S. Provisional Application Ser. No. 63/082,615, filed Sep. 24, 2020, the entire content of which is incorporated herein by reference.

TECHNICAL FIELD

This disclosure generally relates to medical devices, and more specifically, testing implantable medical leads during implantation procedures.

BACKGROUND

Cardiac pacing is delivered to patients to treat a wide variety of cardiac dysfunctions. Cardiac pacing is often delivered by an implantable medical device (IMD). An IMD typically delivers such therapy to the heart via electrodes located on one or more leads, which may be intracardiac or extracardiovascular leads, although leadless IMDs for delivering such therapies have also been implemented.

During normal sinus rhythm (NSR), the heartbeat is regulated by electrical signals produced by the sino-atrial (SA) node located in the right atrial wall. Each intrinsic atrial depolarization signal produced by the SA node spreads across the atria, causing the depolarization and contraction of the atria, and arrives at the atrioventricular (AV) node. The AV node responds by propagating a ventricular depolarization signal through the bundle of His (or "His bundle") of the ventricular septum and thereafter to the bundle branches and the Purkinje muscle fibers of the right and left ventricles. This native ventricular conduction system including the His bundle, right and left bundle branches and the Purkinje fibers may be referred to as the "His-Purkinje conduction system."

Cardiac pacing of the His-Purkinje conduction system has been proposed to provide synchronous ventricular pacing along the heart's native His-Purkinje conduction system (HPCS). Pacing the ventricles via the HPCS allows recruitment along the heart's natural conduction system and is hypothesized to restore physiologically normal rhythm and cardiac activation better than other pacing sites, such as the ventricular apex. Leads proposed for HPCS pacing typically include a fixed or extendable distal electrode that is configured to map or activate the HPCS via the endocardial surface or penetrate into cardiac tissue, such as the intraventricular septum.

SUMMARY

In general, this disclosure is directed to devices and techniques that facilitate guiding a distal electrode fixation of an implantable medical lead, e.g., in situ or in real time, to a desired position/depth on the endocardial surface or within cardiac tissue, such as the intraventricular septum, or other patient tissue. Electrical signals, e.g., real-time electrical signals, sensed via the distal electrode, such as pacing impedance or electrogram signals, may be used to determine whether a current position/depth is adequate. In the case of HPCS, for example, the presence of HPCS features in the cardiac electrogram, such features indicative of the electrical activity of the HPCS, may indicate an adequate distal electrode position.

In some cases, the whole implantable medical lead or a portion thereof is rotated during the implantation procedure to advance/retract a helical or other fixed or extendable electrode within tissue. However, a test device used to collect signals from the distal electrode and its associated cabling may not be configured to rotate with the lead. An adapter according to this disclosure may include a portion of a conductive pathway between the lead and the test device that is rotationally fixed and another portion of the conductive pathway that is rotatable with the lead. For example, the adapter may include a rotational electrical coupling that is configured to electrically connect a lead electrical connector to an adapter electrical connector. The rotational electrical coupling may comprise a first conductive component configured to be electrically connected to the lead electrical connector and rotatable with a proximal portion of the implantable medical lead, and a second conductive component electrically connected to the first conductive component and the adapter electrical connector. The second conductive component may be rotationally fixed. In this manner, a rotatable adapter according to this disclosure may allow a test device to remain connected to an implantable medical lead while implanting/fixing the lead by rotating the lead body.

In some cases, advancement and retraction of the distal electrode may introduce artifacts or other noise into these signals used to determine whether its position/depth is adequate. For example, relative rotation of portions of the conductive path between the electrode and the test device may introduce such noise, e.g., due to make/break events occurring during the relative rotation. The noise may corrupt the signals such that the adequacy of the position/depth of the electrode cannot be determined during rotation. Consequently, the implanting physician may need to frequently stop rotating to test a position before resuming rotation, which may increase the time and effort needed for the implantation procedure.

An adapter according to the present disclosure may include features to reduce the presence of such noise in the signals sensed during rotation of the implantable medical lead, e.g., the signals may be substantially noise-free. For example, the first and second conductive components of the rotational electrical coupling may comprise a material selected for adequate conduction and relatively lower friction, such as graphite or another soft metal, e.g., a metal with a hardness of 1-3 on the Mohs scale of hardness. As another example, the adapter may include an elastically deformable element, such as a spring, configured to maintain the second conductive component in abutment and electrical contact with the first conductive component as the first conductive component moves during rotation. These features may allow an implanting physician to observe relatively noise-free signals, or data derived therefrom, during rotation of the implantable medical lead, which may reduce the time and effort need to identify an adequate implant position/depth for the distal electrode.

In some examples, a system comprises an implantable medical lead and an adapter. The implantable medical lead comprises an electrode at a distal end of the implantable medical lead, and a lead electrical connector at a proximal portion of the implantable medical lead, the lead electrical connector electrically coupled to the electrode. The adapter comprises an adapter body configured to receive the proximal portion of the implantable medical lead, including the lead electrical connector, and allow rotation of the proximal portion relative to the adapter body when the proximal portion is received by the adapter body. The adapter further comprises an adapter electrical connector configured to be electrically connected to a test device, and a rotational electrical coupling within the adapter body, the rotational electrical coupling configured to electrically connect the lead electrical connector to the adapter electrical connector. The rotational electrical coupling comprises a first conductive component configured to be electrically connected to the lead electrical connector and rotatable within the adapter body with the proximal portion of the implantable medical lead, and a second conductive component electrically connected to the first conductive component and the adapter electrical connector, the second conductive component rotationally fixed relative to the adapter body.

In some examples, an adapter is configured to electrically connect a test device to an implantable medical lead. The implantable medical lead comprises an electrode at a distal end of the implantable medical lead, and a lead electrical connector at a proximal portion of the implantable medical lead, the lead electrical connector electrically coupled to the electrode. The adapter comprises an adapter body configured to receive the proximal portion of the implantable medical lead, including the lead electrical connector, and allow rotation of the proximal portion relative to the adapter body when the proximal portion is received by the adapter body. The adapter further comprises an adapter electrical connector configured to be electrically connected to a test device, and a rotational electrical coupling within the adapter body, the rotational electrical coupling configured to electrically connect the lead electrical connector to the adapter electrical connector. The rotational electrical coupling comprises a first conductive component configured to be electrically connected to the lead electrical connector and rotatable within the adapter body with the proximal portion of the implantable medical lead, and a second conductive component electrically connected to the first conductive component and the adapter electrical connector, the second conductive component rotationally fixed relative to the adapter body.

In some examples, a method comprises receiving, by an adapter, a proximal portion of an implantable medical lead, the implantable medical lead comprising an electrode at a distal end of the implantable medical lead, and a lead electrical connector at the proximal portion of the implantable medical lead, the lead electrical connector electrically coupled to the electrode. The method further comprises rotating, by the implantable medical lead, to advance the electrode for implantation in patient tissue. The adapter comprises an adapter body configured to receive the proximal portion of the implantable medical lead, including the lead electrical connector, and allow rotation of the proximal portion relative to the adapter body when the proximal portion is received by the adapter body, and a rotational electrical coupling within the adapter body, the rotational electrical coupling configured to electrically connect the lead electrical connector to the adapter electrical connector. The rotational electrical coupling comprises a first conductive component configured to be electrically connected to the lead electrical connector and rotatable within the adapter body with the proximal portion of the implantable medical lead, and a second conductive component electrically connected to the first conductive component and the adapter electrical connector, the second conductive component rotationally fixed relative to the adapter body. The method further comprises receiving, by a test device electrically coupled to the adapter, signals sensed via the electrode during the rotation of the implantable medical lead.

In some examples, a method of making an adapter configured to electrically connect a test device to an implantable medical lead comprises attaching a lead receptacle to a first conductive component, attaching a test device connector to a second conductive component, and forming an adapter body around the first and second conductive component, and at least portions of the lead receptacle and the test device connector. The first conductive component and the lead receptacle are rotatable relative to the adapter body, and the second conductive component and the test device connector are rotationally fixed relative to the adapter body.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
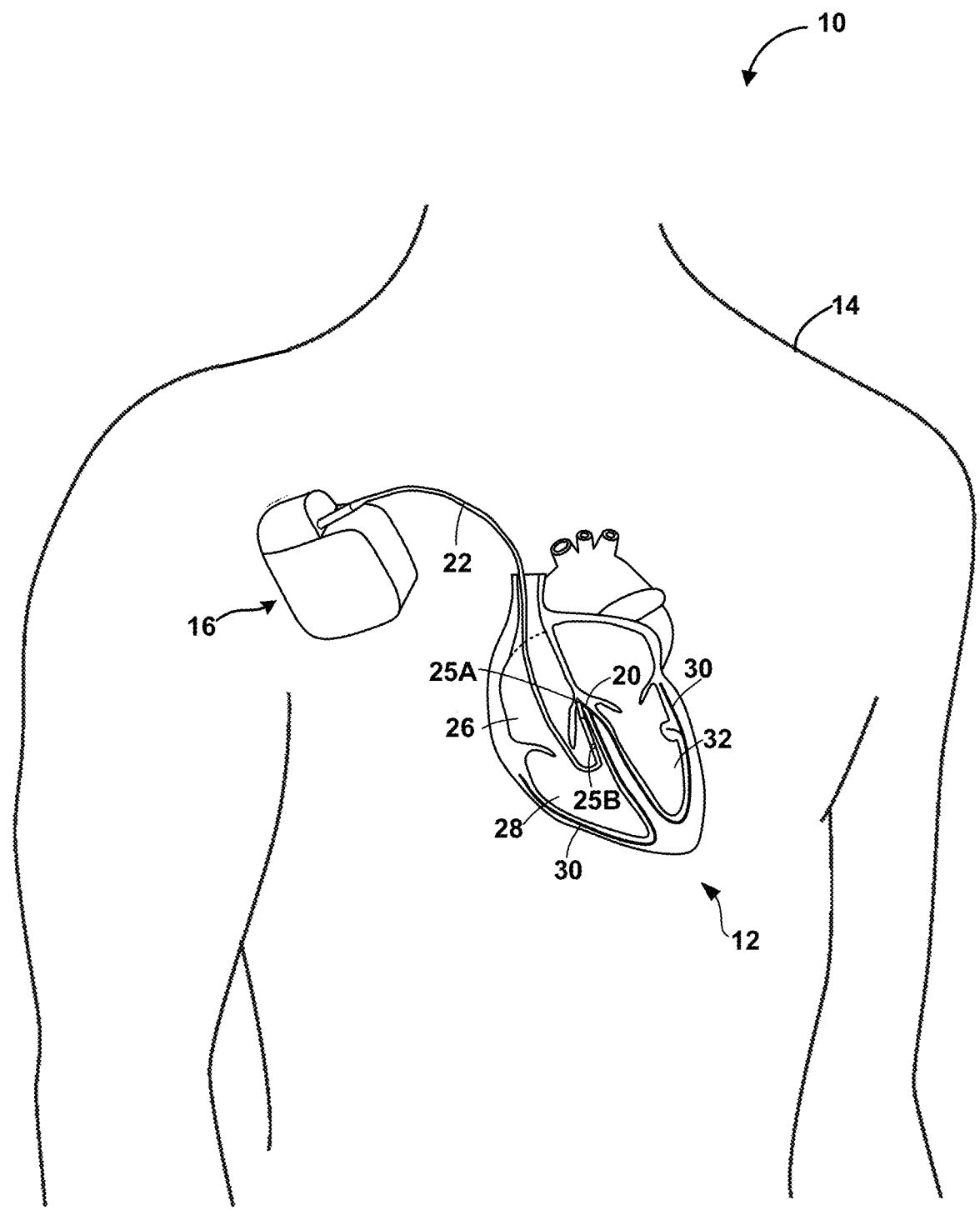
FIG. 1 is a conceptual diagram illustrating an example medical device system, including an example implantable medical lead, for delivering conduction system pacing to a patient.

FIG. 1 is a conceptual diagram illustrating an example medical device system 10 for delivering HPCS pacing to a heart 12 of a patient 14. As illustrated by example system 10 in FIG. 1, system 10 may include an implantable medical device (IMD) 16 with cardiac pacing capabilities. 1 MB 16 is connected to an implantable medical lead 22. 1 MB 16 senses electrical signals attendant to the depolarization and repolarization of heart 12, e.g., a cardiac EGM, via electrodes on one or more of lead 22 and/or the housing of IMD 16. IMD 16 may also deliver therapy in the form of electrical signals, e.g., cardiac pacing, to heart 12 via electrodes located on lead 22. In the illustrated example, lead 22 includes a distal electrode 25A at a distal end of lead 22 and a proximal electrode 25B located proximally of the distal end (collectively, "electrodes 25"). In other examples, lead may include more or fewer electrodes 25, such as examples in which lead 22 includes only electrode 25A.

Lead 22 extends into heart 12 of patient 14 to sense electrical activity of heart 12 and/or deliver electrical stimulation to heart 12. In the example shown in FIG. 1, lead 22 extends through one or more veins (not shown), the superior vena cava (not shown), and right atrium 26, and into right ventricle 28. System 10 may include additional leads coupled to IMD 16, such as a left ventricular (LV) lead that extends through one or more veins, the vena cava, right atrium 26, and into the coronary sinus to a region adjacent to the free wall of left ventricle 32 of heart 12, and/or a lead that extends into right atrium 26.

Lead 22, e.g., distal electrode 25A, is positioned to provide pacing to the HPCS. Providing HPCS pacing is sometimes referred to as "His-Purkinje pacing." In the illustrated example, lead 22 is positioned to provide pacing to His-Purkinje 20 between an atrioventricular bundle (not shown) and branches of Purkinje fibers 30. In other examples, lead 22 and distal electrode 25A may be implanted at positions to provide pacing to other portions of the HPCS, such as a left bundle branch (LBB) or right bundle branch (RBB).

Distal electrode 25A may be extended from a distal end of lead 22 and into cardiac tissue. Distal electrode 25A may take the form of a fixed helix, an extendable helix, or tine tip electrode, in some examples. Electrode 25B may take the form of a ring electrode electrically insulated from electrode 25A. In some examples, each of electrodes 25A and 25B is electrically coupled to a respective conductor within the body of lead 22 and thereby coupled to circuitry within IMD 16.

Distal electrode 25A may be positioned within the cardiac tissue such that pacing stimulation delivered via distal electrode 25A activates the HPCS. During an implantation procedure for lead 22, an implanting physician may position a distal end of lead at a desired location, and fix distal electrode 25A distally from the distal end of lead 22 to a desired depth within the cardiac tissue, e.g., the intraventricular myocardium.

Figure 2:
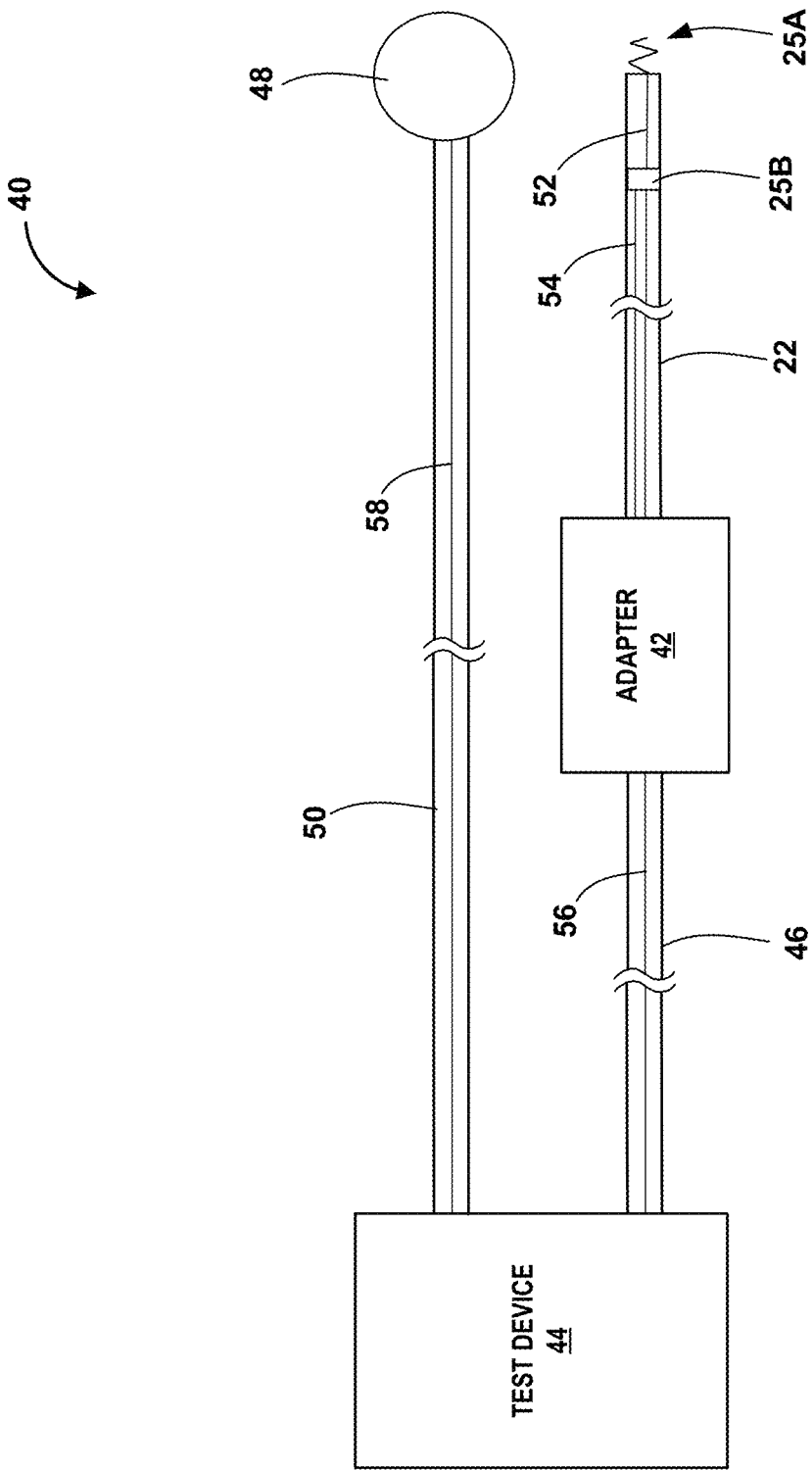
FIG. 2 is a conceptual diagram illustrating an example system for testing the implantable medical lead of FIG. 1 during an implantation procedure, the example system including a rotatable adapter to connect the implantable medical lead to a test device.

FIG. 2 is a conceptual diagram illustrating an example system 40 for testing implantable medical lead 22 during an implantation procedure. As illustrated by the example of FIG. 2, system 40 may include a rotatable adaptor 42 configured to connect implantable medical lead 22 to a test device 44. In the illustrated example, adapter 42 is selectively connected to test device 44 via a cable 46, although other selective or permanent connections between adapter 42 and test device 44 are possible. System 40 also includes an auxiliary electrode 48, which may be attached externally to patient 14, e.g., via an adhesive patch. Auxiliary electrode 48 may be connected to test device 44 via a cable 50.

As illustrated by the example of FIG. 2, lead 22 includes a conductor 52 electrically connected to distal electrode 25A and a conductor 54 electrically connected to proximal electrode 25B. As will be discussed in greater detail below, conductor 52 is electrically connectable to adapter 42. Cable 46 includes a conductor 56 which is electrically connected or connectable to both adapter 42 and test device 44. When lead 22, adapter 42, cable 46, and test device 44 are connected, conductors 52 and 56 electrically connect distal electrode 25A to test device 44. Auxiliary electrode 48 is also connected or connectable to test device 44 via conductor 58 of cable 50. In the illustrated example, adapter 42 may be referred to as a unipolar adapter, because it is configured to electrically connect one electrode of lead 22, distal electrode 25A, to test device 44. In other examples, adapter 42 may be a bipolar adapter, e.g., as shown and described with respect to FIGS. 6A-6B, configured to connect both electrodes 25 to test device 44 and, in such examples, electrodes 25 may act as a bipolar pair during testing as described herein, and auxiliary electrode 48 and cable 50 may be omitted.

Test device 44 receives one or more signals sensed using distal electrode 25A with auxiliary electrode 48 acting as a reference electrode. In some examples, test device 44 measures a pacing impedance signal using distal electrode 25A. In some examples, test device 44 receives a cardiac electrogram signal sensed using distal electrode 25A with auxiliary electrode 48 acting as a reference electrode. An implanting physician may use the signals and/or values derived from the signals to determine whether a current position/depth of distal electrode 25A is adequate for sensing and therapy delivery by IMD 16 via distal electrode 25A. In the case of HPCS pacing, for example, the presence of HPCS features in the cardiac electrogram, such features indicative of the electrical activity of the His bundle or bundle branches, may indicate an adequate position/depth of distal electrode 25A.

In some cases, implantable medical lead 22, or a portion thereof, is rotated during the implantation procedure to advance/retract distal electrode 25A, e.g., relative to tissue of patient 14. However, test device 44 and cable 46 may not be able to rotate with lead 22. To facilitate rotation of lead 22 relative to test device 44 and cable 46, adapter 42 includes a portion of a conductive pathway that is rotationally fixed, like cable 46, and another portion of the conductive pathway that is rotatable with lead 22, as discussed in greater detail with respect to FIGS. 3A-3C.

In some cases, advancement and retraction of distal electrode 25A may introduce artifacts or other noise into the signals used to determine whether its position/depth is adequate. For example, relative rotation of portions of the conductive through adapter 25A may introduce such noise, e.g., due to make/break events occurring during the relative rotation. The noise may corrupt the signals such that the adequacy of the position/depth of electrode 25A cannot be determined during rotation. Consequently, the implanting physician may need to frequently stop rotating to test a position before resuming rotation, which may increase the time and effort needed for the implantation procedure. Adapter 42 may include features to reduce the presence of such noise in the signals sensed during rotation of implantable medical lead 22, as discussed in further detail with respect to FIGS. 3A-3C.

Figure 3A:
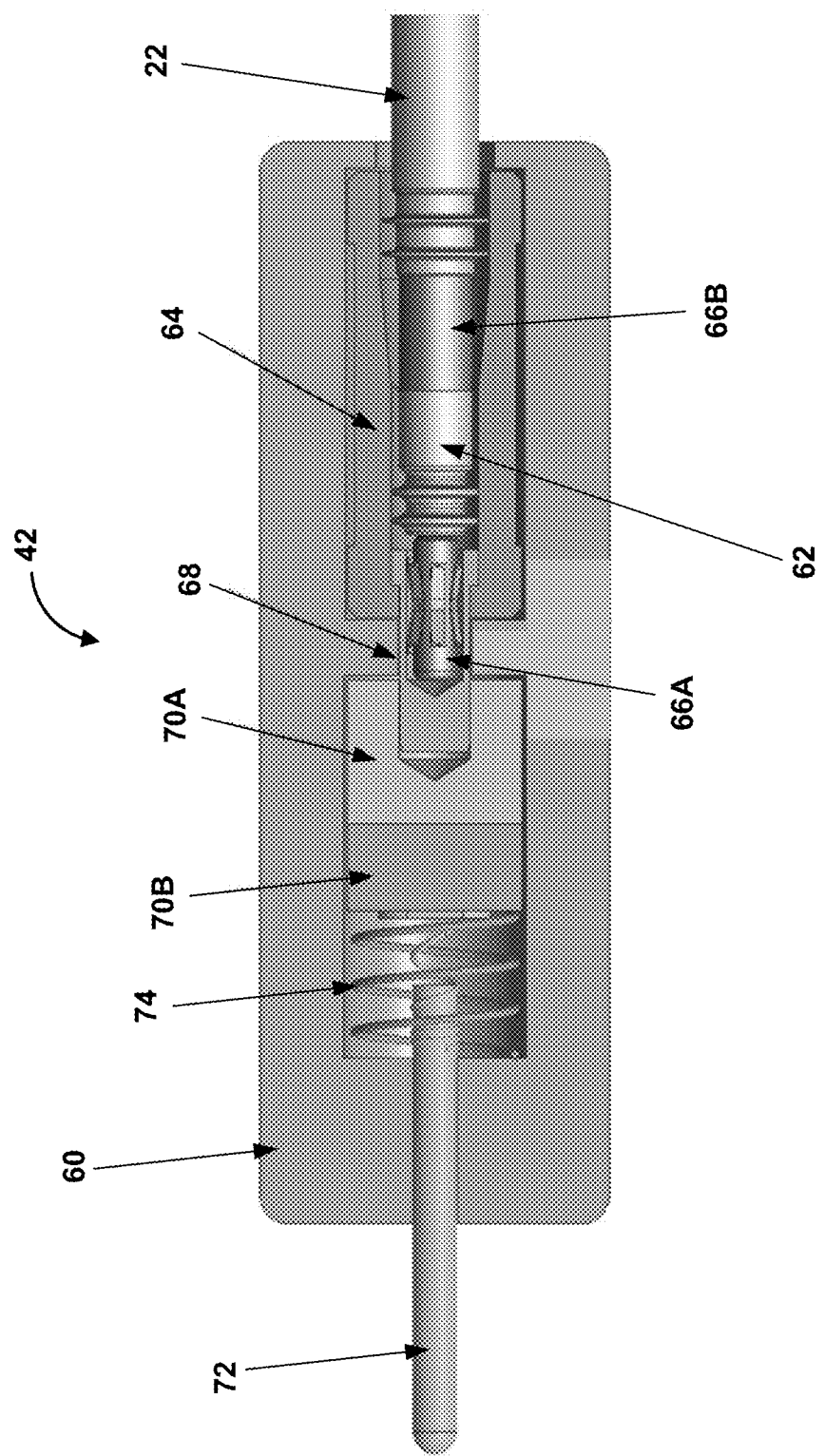
FIG. 3A is cross-sectional diagram illustrating an example configuration of the rotatable adapter of FIG. 2.
Figure 3B:
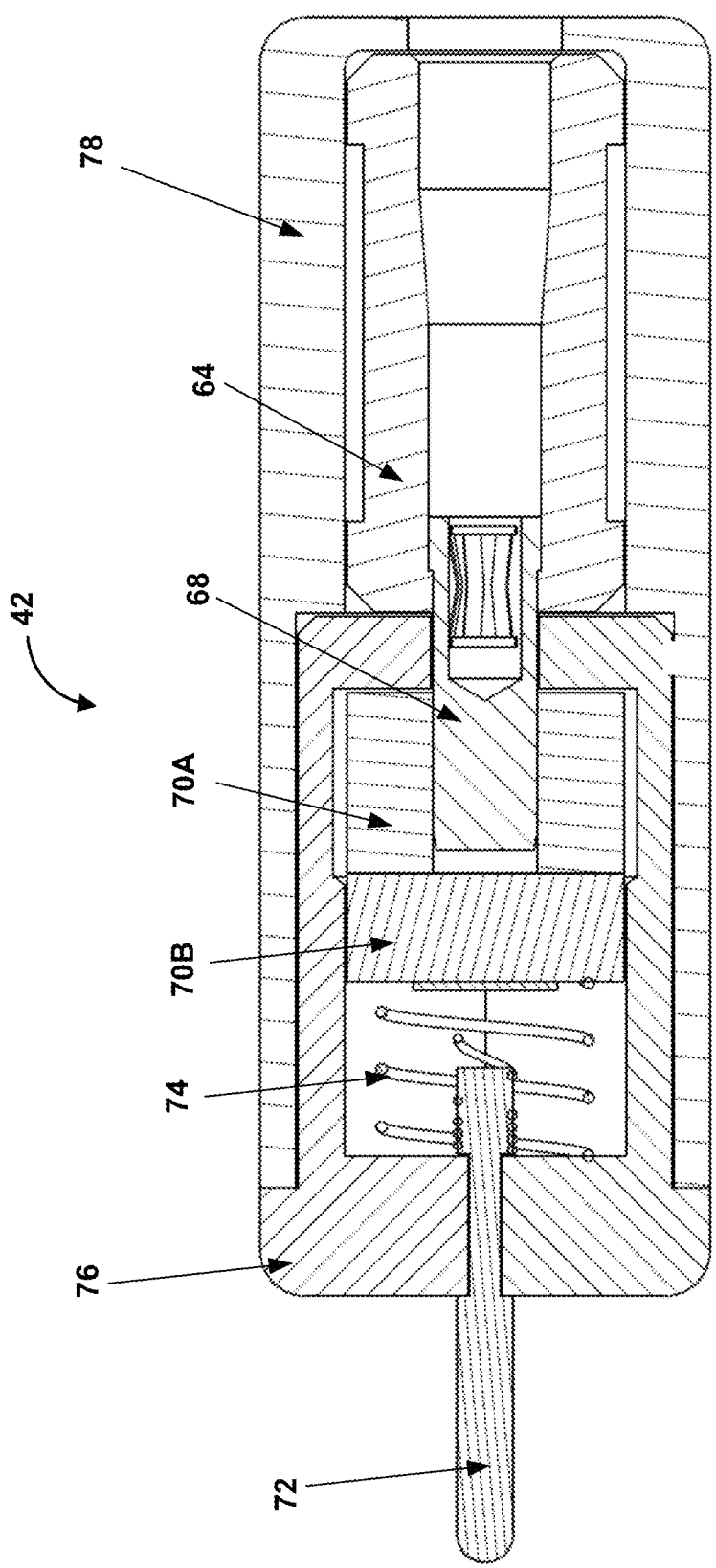
FIG. 3B is cross-sectional diagram illustrating another example configuration of the rotatable adapter of FIG. 2.
Figure 3C:
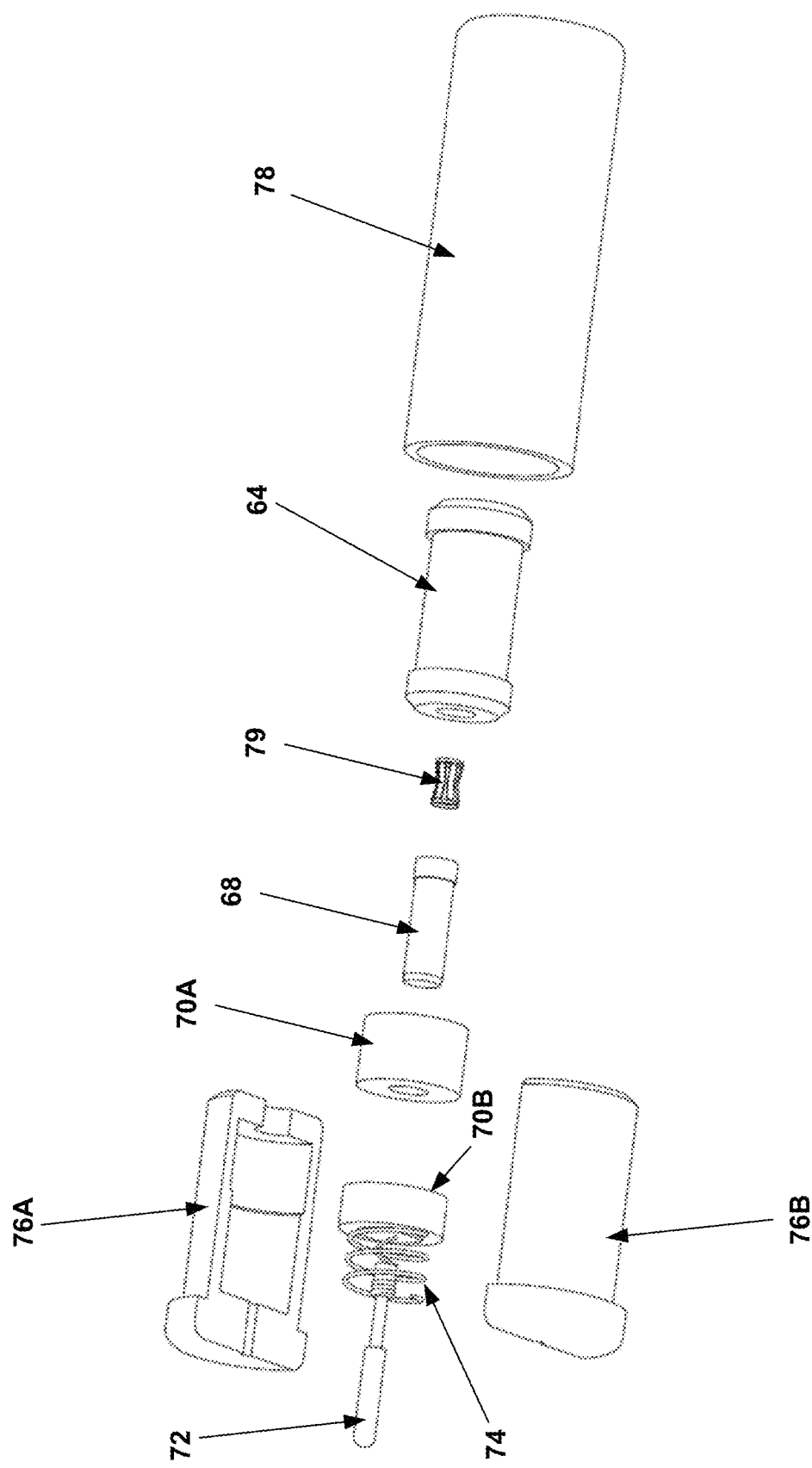
FIG. 3C is an exploded diagram illustrating an example configuration of the rotatable adapter of FIG. 2.

FIGS. 3A-3C are diagrams illustrating an example configuration of rotatable adapter 42. FIGS. 3A and 3B are cross-sectional diagrams, with FIG. 3A illustrating adapter 42 interacting with lead 22, and FIG. 3C is an exploded view of adapter 42. In the example illustrated by FIGS. 3A-3C, adapter 42 includes an adapter body 60 that defines cavities configured to receive and/or house the various components of adapter 42, as well as to receive a proximal portion 62 of lead 22. In some examples, adapter body 60 is molded or otherwise formed around an assembly of the other components of adapter 42. In other examples, the outer body of adapter body 60 may be separately formed and then assembled around an assembly of the other components of adapter 42.

Adapter body 60 houses an electrically insulative bearing 64 defining a channel configured to receive proximal portion 62 of lead 22. Insulative bearing 64 may be formed from polyether ether ketone (PEEK) or other materials, e.g., having similar properties to PEEK. Insulative bearing 64 may be configured to retain proximal portion 62 of lead 22, e.g., with a friction fit, and to rotate within adapter body 60 with proximal portion 62 of lead 22. As illustrated in FIG. 3A, proximal portion 62 of lead 22 may include a first lead electrical connector 66A connected to distal electrode 25A by conductor 52 (FIG. 2), and a second lead electrical connector 66B connected to proximal electrode 25B by conductor 54 (FIG. 2).

Adapter body 60 also houses an electrical contact 68 configured to be electrically connected to lead electrical connector 66A, which is electrically connected to distal electrode 25A. In the illustrated example, electrical contact 68 is configured to receive a portion of proximal portion 62 of lead 22. Electrical contact 68 may, in some examples, be a multi-beam electrical contact, e.g., as described in U.S. Pat. No. 4,764,132.

At least a portion of electrical contact 68 may be received within the channel defined by insulative bearing 64. In some examples, electrical contact 68 may be bonded to insulative bearing 64. Electrical contact 68 may be configured to rotate with insulative bearing 64, and thereby rotate within adapter body 60 with proximal portion 62 of lead 22.

Adapter body 60 also houses a first conductive component 70A and a second conductive component 70B (collectively, "conductive components 70"). First conductive component 70A is electrically connected and bonded to electrical contact 68. First conductive component 70A may be configured to rotate with electrical contact 68, insulative bearing 64, and proximal portion 62 of lead 22 within adapter body 60. In the illustrated example, first conductive component 70 defines a recess configured to receive a portion of electrical contact 68.

First conductive component 70A is also electrically connected to second conductive component 70B. However, conductive components 70 are not bonded to each other. In some examples, second conductive component 70B is rotationally fixed within adapter body 60. Second conductive component 70B does not rotate with proximal portion 62 of lead 22. As illustrated in FIG. 3A, conductive components 70 may be electrically connected by physically contact each other, e.g., being adjacent to each other and/or physically abutted to each other.

Second conductive component 70B is also electrically connected to, and in some cases bonded to, an adapter electrical connector 72. Adapter electrical connector 72 is configured to extend from adapter body 60 and allow an electrical connection of adapter 42 to test device 44, e.g., via cable 46 (FIG. 2). Adapter electrical connector 72 may also be rotationally fixed relative to adapter body 60. Collectively, electrical contact 68, conductive components 70, and adapter electrical connector 72 may define a rotational electrical coupling in which a portion of the electrical path is configured to rotate with lead 22, and another portion of the electrical path is rotationally fixed.

As indicated above, adapter 42 may include features to mitigate noise that could otherwise be introduced into the signals received by test device 44 via distal electrode 25A during rotation of lead 22. For example, conductive components 70 may comprise a material selected for adequate conduction and relatively lower friction, such as graphite, other soft metals, e.g., metals with a hardness of 1-3 on the Mohs scale of hardness, or materials that include graphite and/or soft metals. Other example soft metals include tin, gold, silver, or copper. In some examples, conductive components 70 may comprise the material, e.g., be coated with the material. In some examples, conductive components 70 may consist essentially of the material, e.g., may include other materials that do not materially affect the properties of conductive components 70, such as properties related to electrical conduction and friction. The material may facilitate relatively consistent electrical contact between conductive components 70 as the conductive components rotate relative to each other.

Additionally, as illustrated by the example of FIG. 3A, adapter 42 may include an elastically deformable element 74, such as a spring, configured to maintain second conductive component 70B in electrical contact, e.g., in abutment, with first conductive component 70A as the first conductive component moves during rotation of lead 22. The likelihood of noise in the signals received by test device 44 from distal electrode 25A may be reduced as the consistency of electrical and physical contact between conductive components 70 during relative rotation increases. These features, e.g., the material of conductive components 70 and elastically deformable element 74, may allow an implanting physician to observe relatively noise-free signals, or data derived therefrom, during rotation of implantable medical lead 22, which may reduce the time and effort need to identify an adequate implant position/depth for distal electrode 25A.

As illustrated by FIG. 3C, the outer body of adapter body 60 can be separately formed and then assembled around an assembly of the other components of adapter 42. For example, the outer body of adapter body may include a first distal outer body component 76A, a second distal outer body component 76B (collectively, distal outer body component 76), and a proximal outer body component 78. Distal outer body component 76 and proximal outer body component 78 may be separately formed and then assembled to form adapter body 60 around an assembly of the other components of adapter 42. As illustrated in FIG. 3C, rotatable adapter may comprise a multi-beam connector portion 79 of lead electrical connector 66A or lead electrical connecter 66B to facilitate multi-beam electrical contact, e.g., as described in U.S. Pat. No. 4,764,132.

Figure 4:
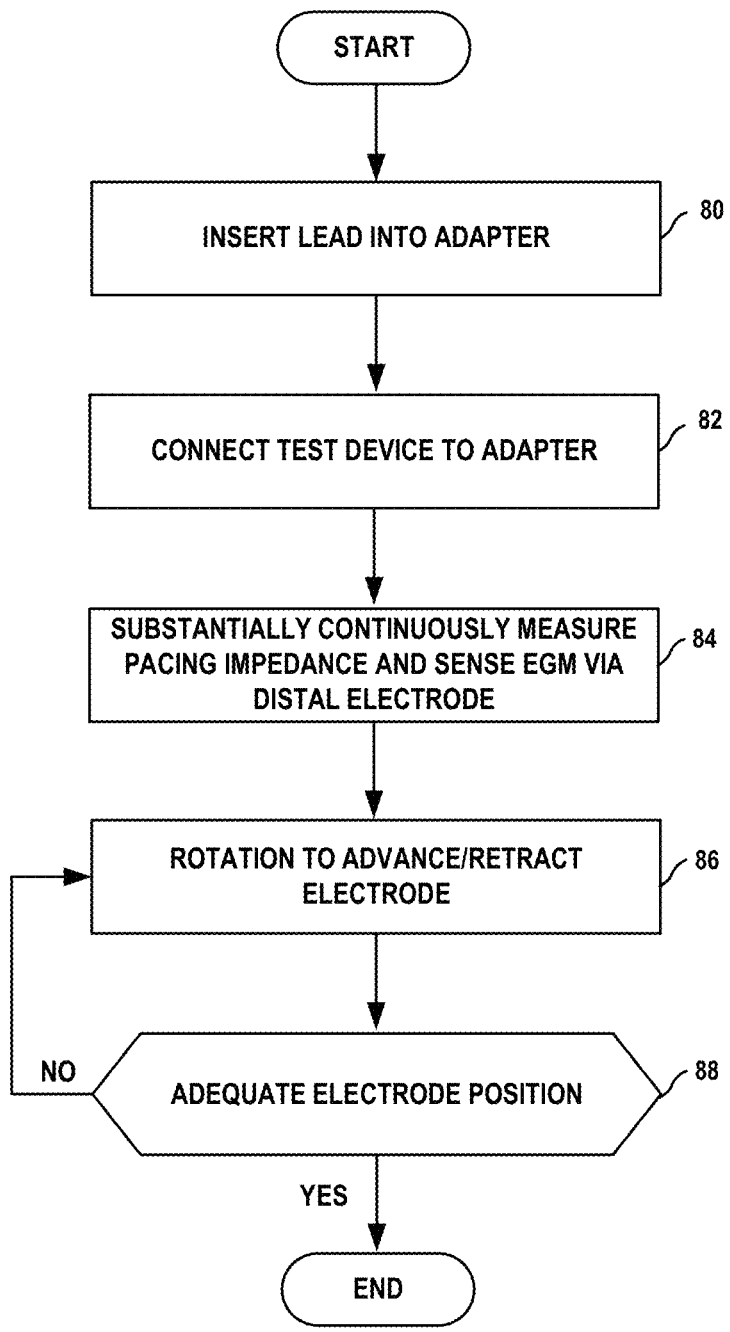
FIG. 4 is a flow diagram illustrating an example technique for testing an implantable medical lead during an implantation procedure using the rotatable adapter of FIGS. 2 and 3A-C.

FIG. 4 is a flow diagram illustrating an example technique for testing implantable medical lead 22 during an implantation procedure using rotatable adapter 42. According to the example of FIG. 4, lead 22 is inserted into adapter 42 (80). For example, proximal portion 62 of lead 22 may be inserted into a receptacle or channel defined by adapter body 60, insulative bearing 64, and/or electrical contact 68, as illustrated in FIGS. 3A-3C. When proximal portion 62 of lead 22 is received by adapter 42, distal electrode 25A may be electrically connected to electrical contact 68 via conductor 52 and lead electrical connector 66A.

The example technique of FIG. 4 further includes connecting test device 44 to adapter 42, e.g., via cable 46 (82). In some examples, cable 46 comprises an alligator clip or other connector configured to engage a portion of adapter connector 72 that extends from adapter body 60. With proximal portion 62 of lead 22 inserted into adapter 42 and test device 44 connected to adapter 42, distal electrode 25A of lead 22 is electrically connected to test device 44 via a rotation electrical coupling as described herein.

A distal end of lead 22 may be positioned adjacent to cardiac tissue, e.g., the intraventricular septum, at a desired location for sensing and delivery of therapy by IMD 16, e.g., for HPCS pacing. The distal end of lead 22 may be positioned before or after one or both of inserting proximal portion 62 of lead 22 into adapter 42 and connecting test device 44 to adapter 42.

With distal electrode 25A electrically connected to test device 44 and located as desired relative to the cardiac tissue, test device 44 may begin to measure impedance and sense a cardiac EGM via distal electrode 25A (84). Once initiated, the measurement and sensing by test device 44 may be substantially continuous, e.g., at a sampling rate during a period of time that includes a plurality of cardiac cycles and a plurality of positions/depths of distal electrode 25A. While test device 44 measures or senses one or more signals, lead 22 or a portion thereof may be rotated to advance and/or retract distal electrode 25A within cardiac tissue (86). In some cases, distal electrode 25A may additionally be repositioned to different entry points of and trajectories through cardiac tissue.

Based on an output of test device 44 that is based on the one or more signals obtained via distal electrode 25A, the implanting physician may determine whether a current position/depth of distal electrode 25A is adequate for the sensing and delivery of therapy by IMD 16 (88). If the current position/depth is not adequate (NO of 88), then the physician may continue to rotate lead 22 to advance/retract distal electrode 25A (86) relative to tissue of heart 12 while test device 44 continues to acquire one or more signals via distal electrode 25A. If the current position/depth is adequate (YES of 88), then the physician may end that portion of an implantation procedure for IMD 16 and lead 22.

Figure 5:
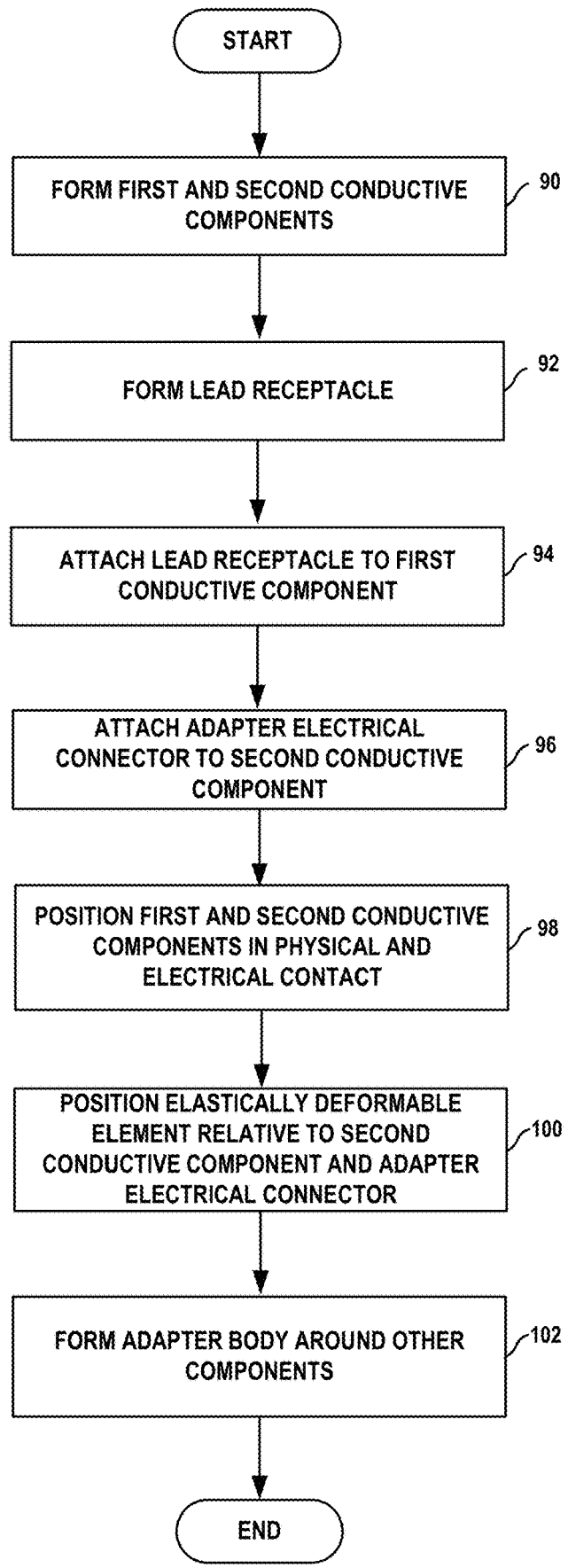
FIG. 5 is a flow diagram illustrating an example technique for making the rotatable adapter of FIGS. 2 and 3A-3C.

FIG. 5 is a flow diagram illustrating an example technique for making rotatable adaptor 42. The example of FIG. 5 includes forming first and second conductive components 70, e.g., to comprise graphite as described above (90). The example further comprises forming a lead receptacle configured to receive proximal portion 62 of lead 22, e.g., by forming and assembling insulative bearing 64 and electrical contact 68 as described above (92). The example further comprises attaching, e.g., electrically connecting and bonding, the lead receptacle, e.g., electrical contact 68, to first conductive component 70A (94).

The example technique of FIG. 5 further includes attaching e.g., electrically connecting and bonding, adapter electrical connector 72 to second conductive component 70B (96). The example technique further comprises positioning first and second conductive components 70 in physical and electrical contact, e.g., in abutment (98), and positioning elastically deformable element 74 relative to second conductive component 70B and, in some cases, adapter electrical connector 72 (100). The example technique further comprises forming adapter body 60 around the other components of adapter 42, e.g., by molding, assembly, and/or other processes (102).

Figure 6A:
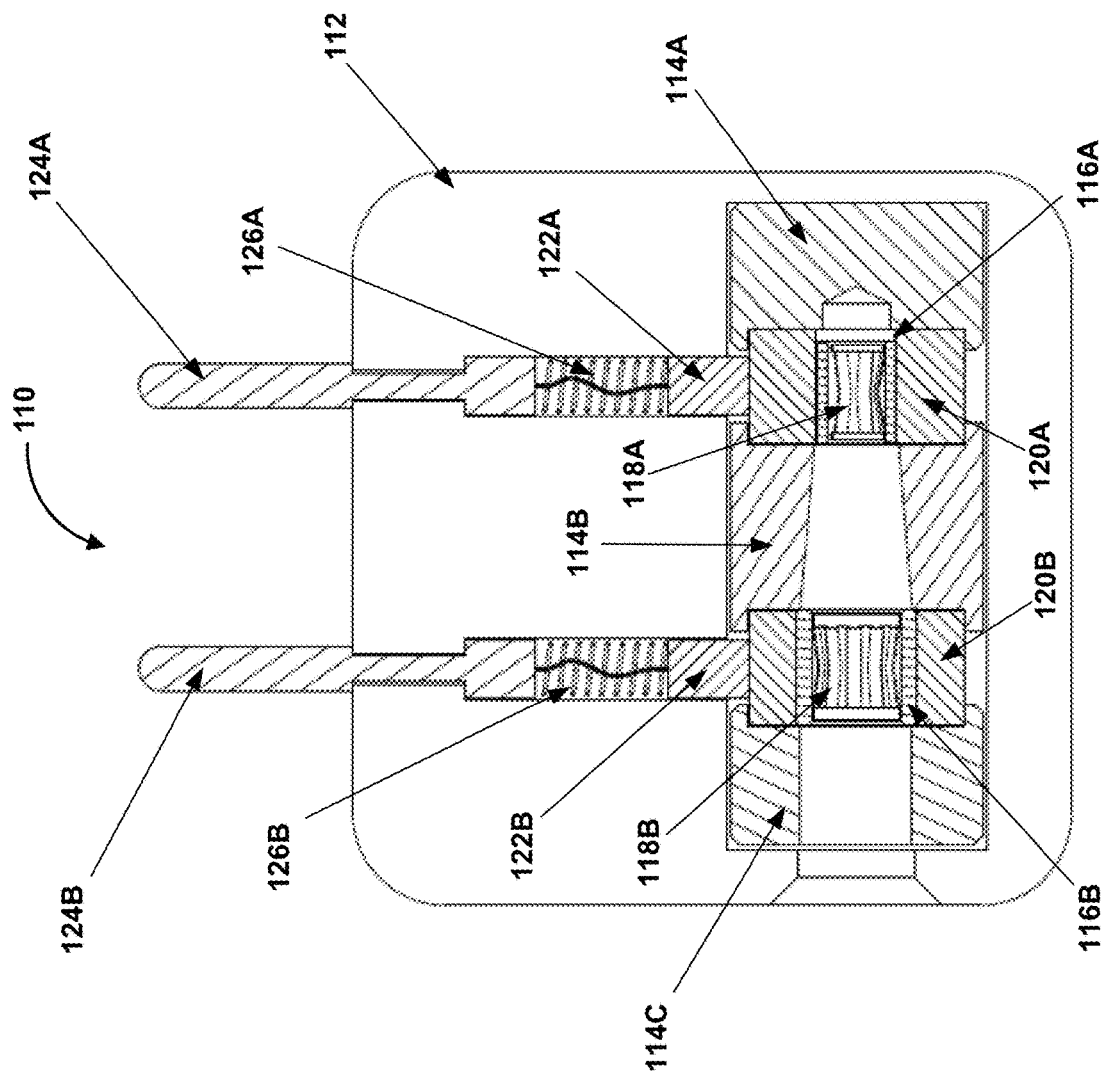
FIG. 6A is a cross-sectional diagram illustrating an example configuration of a rotatable adapter configured to electrically connect a proximal electrode and a distal electrode of an implantable medical lead to a test device.
Figure 6B:
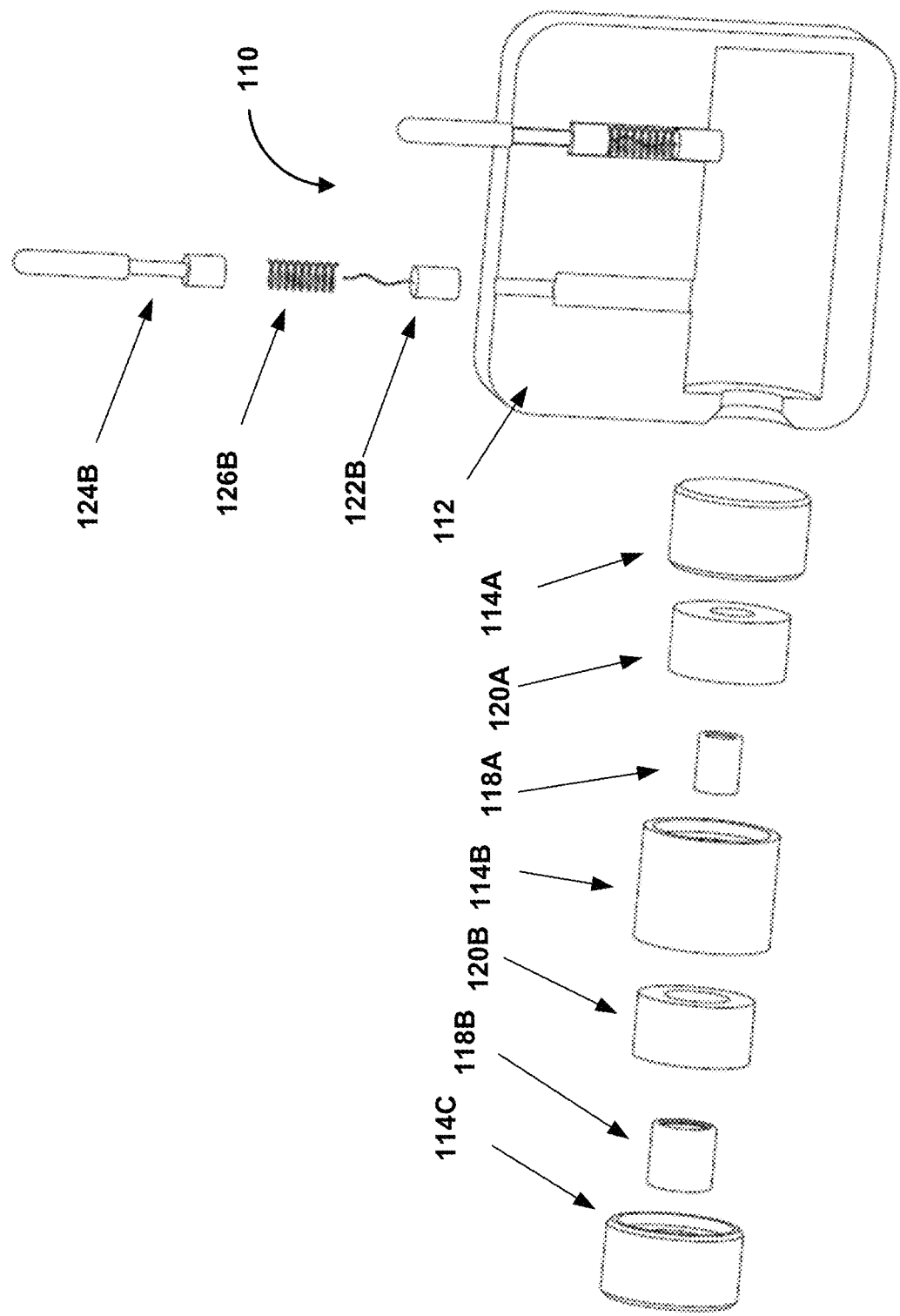
FIG. 6B is an exploded diagram illustrating an example configuration of a rotatable adapter configured to electrically connect a proximal electrode and a distal electrode of an implantable medical lead to a test device.

FIGS. 6A and 6B are diagrams illustrating an example configuration of a bipolar adapter 110. FIG. 6A is a cross-sectional diagram and FIG. 6B is an exploded diagram. In the example illustrated by FIGS. 6A and 6B, bipolar adapter 110 includes a bipolar adapter body 112 that defines cavities configured to receive and/or house the various components of bipolar adapter 110 as well as to receive a proximal portion 62 of lead 22. In some examples, bipolar adapter body 112 is molded or otherwise formed around an assembly of the other components of bipolar adapter 110. In other examples, the outer body of adapter body 112 may be separately formed and then assembled around an assembly of the other components of adapter 110.

Bipolar adapter body 112 houses a first electrically insulative bearing 114A, a second electrically insulative bearing 114B, and a third electrically insulative bearing 114C (collectively, "insulative bearings 114"). Collectively, insulative bearings 114 define a channel configured to receive proximal portion 62 of lead 22. Insulative bearings 114 may be formed from polyether ether ketone (PEEK) or other materials, e.g., having similar properties to PEEK. Insulative bearings 114 may be configured to retain proximal portion 62 of lead 22, e.g., with a friction fit, and to rotate within bipolar adapter body 112 with proximal portion 62 of lead 22.

Adapter body 112 also houses a first electrical contact 116A and a second electrical contact 116B (collectively, "electrical contacts 116"). The first electrical contact 116A is configured to be electrically connected to a first lead electrical connector, which is electrically connected to distal electrode 25A. The second electrical contact 116B is configured to be electrically connected to a second lead electrical connector, which is electrically connected to proximal electrode 25B. In the illustrated example, electrical contacts (116) are configured to receive a portion of proximal portion 62 of lead 22. Electrical contacts 116 may be multi-beam electrical contacts, e.g., as described in U.S. Pat. No. 4,764,132. For example, as illustrated in FIGS. 6A and 6B, electrical contacts 116A and 116 may include multi-beam portions 118A and 118B, respectively.

As illustrated in FIG. 6A, at least a portion of electrical contacts 116 may be received within the channel defined by insulative bearings 114. In some examples, electrical contacts 116 may be bonded to insulative bearings 114. Electrical contacts 116 may be configured to rotate with insulative bearings 114, and thereby rotate within adapter body 112 with proximal portion 62 of lead 22.

Adapter body 112 can additionally house or be connected to first conductive components 120A and 120B (collectively, "first conductive components 120"), and second conductive components 122A and 122B (collectively, "second conductive components 122"). Bipolar adapter 110 further comprises adapter electrical connectors 124A and 124B (collectively, "adapter electrical connectors 124") and deformable elements 126A and 126B collectively, "deformable elements 126"). Electrical contacts 116, first conductive components 120, second conductive components 122 and adapter electrical connectors 124 may define respective rotational electrical couplings for each of electrodes 25 of lead 22, in which a portion of the electrical path is configured to rotate with lead 22, and another portion of the electrical path is rotationally fixed.

Although described in the context of a unipolar adapter (FIGS. 2 and 3A-3C) and a bipolar adapter (FIGS. 6A and 6B), the techniques of this disclosure may be implemented in an adapter configured to connect any number of electrodes on a lead to a test device. For example, an adapter configured according to the techniques of this invention may be a quadripolar adapter configured to connect four electrodes of a lead to a test device.

The present disclosure includes the following examples.

Example 1: A system includes an implantable medical lead includes an electrode at a distal end of the implantable medical lead; and a lead electrical connector at a proximal portion of the implantable medical lead, the lead electrical connector electrically coupled to the electrode; and an adapter includes an adapter body configured to receive the proximal portion of the implantable medical lead, including the lead electrical connector, and allow rotation of the proximal portion relative to the adapter body when the proximal portion is received by the adapter body; an adapter electrical connector configured to be electrically connected to a test device; and a rotational electrical coupling within the adapter body, the rotational electrical coupling configured to electrically connect the lead electrical connector to the adapter electrical connector and includes a first conductive component configured to be electrically connected to the lead electrical connector and rotatable within the adapter body with the proximal portion of the implantable medical lead; and a second conductive component electrically connected to the first conductive component and the adapter electrical connector, the second conductive component rotationally fixed relative to the adapter body.

Example 2: The system of example 1, wherein the second conductive component abuts the first conductive component.

Example 3: The system of example 2, wherein the adapter includes an elastically deformable element within the adapter body, the elastically deformable element configured to maintain the second conductive component in abutment with the first conductive component as the first conductive component moves axially within the adapter body.

Example 4: The system of example 3, wherein the elastically deformable element includes a spring.

Example 5: The system of any of examples 1-4, wherein the first conductive component and the second conductive component include a soft metal.

Example 6: The system of example 5, wherein the first conductive component and the second conductive component include graphite.

Example 7: The system of example 6, wherein the first conductive component and the second conductive component consist essentially of graphite.

Example 8: The system of any of examples 1-7, wherein the rotational electrical coupling includes a contact configured to receive and be electrically connected with the lead electrical connector, wherein the contact is configured to rotate within the adapter body with the proximal portion of the implantable medical lead.

Example 9: The system of example 8, wherein first conductive component is bonded to the contact.

Example 10: The system of example 8 or 9, wherein the rotational electrical coupling includes an insulative bearing defining a channel configured to receive the proximal portion of the implantable medical lead and at least a portion of the contact, wherein the insulative bearing is configured to rotate within the adapter body with the proximal portion of the implantable medical lead.

Example 11: The system of example 10, wherein the insulative bearing is bonded to the contact.

Example 12: The system of any of examples 1-11, wherein the electrode is extendable/retractable from the distal end of the implantable medical lead by rotation of the implantable medical lead.

Example 13: The system of any of examples 1-12, wherein the electrode includes a helix.

Example 14: The system of any of examples 1-13, wherein the rotational electrical coupling is configured to conduct a cardiac electrogram signal in which His-Purkinje conduction system features can be detected during rotation of the implantable medical lead.

Example 15: The system of any of examples 1-14, wherein the electrode includes a first electrode, the lead electrical connector includes a first lead electrical connector, the adapter electrical connector includes a first adapter electrical connector, and the rotational electrical coupling includes a first rotational electrical coupling, wherein the implantable medical lead further includes a second electrode located proximally of the distal end of the implantable medical lead and electrically connected to a second lead electrical connector, and wherein the adapter further includes a second rotational electrical coupling within the adapter body, the second rotational electrical coupling configured to electrically connect the lead electrical connector to a second adapter electrical connector.

Example 16: An adapter configured to electrically connect a test device to an implantable medical lead, the implantable medical lead includes an adapter body configured to receive the proximal portion of the implantable medical lead, including the lead electrical connector, and allow rotation of the proximal portion relative to the adapter body when the proximal portion is received by the adapter body; an adapter electrical connector configured to be electrically connected to the test device; and a rotational electrical coupling within the adapter body, the rotational electrical coupling configured to electrically connect the lead electrical connector to the adapter electrical connector and includes a first conductive component configured to be electrically connected to the lead electrical connector and rotatable within the adapter body with the proximal portion of the implantable medical lead; and a second conductive component electrically connected to the first conductive component and the adapter electrical connector, the second conductive component rotationally fixed relative to the adapter body.

Example 17: The adapter of example 16, wherein the second conductive component abuts the first conductive component.

Example 18: The adapter of example 17, further including an elastically deformable element within the adapter body, the elastically deformable element configured to maintain the second conductive component in abutment with the first conductive component as the first conductive component moves axially within the adapter body.

Example 19: The adapter of example 18, wherein the elastically deformable element includes a spring.

Example 20: The adapter of any of examples 16-19, wherein the first conductive component and the second conductive component include a soft metal.

Example 21: The adapter of example 20, wherein the first conductive component and the second conductive component include graphite.

Example 22: The adapter of example 21, wherein the first conductive component and the second conductive component consist essentially of graphite.

Example 23: The adapter of any of examples 16-22, wherein the rotational electrical coupling includes a contact configured to receive and be electrically connected with the lead electrical connector, wherein the contact is configured to rotate within the adapter body with the proximal portion of the implantable medical lead.

Example 24: The adapter of example 23, wherein first conductive component is bonded to the contact.

Example 25: The adapter of example 23 or 24, wherein the rotational electrical coupling includes an insulative bearing defining a channel configured to receive the proximal portion of the implantable medical lead and at least a portion of the contact, wherein the insulative bearing is configured to rotate within the adapter body with the proximal portion of the implantable medical lead.

Example 26: The adapter of example 25, wherein the insulative bearing is bonded to the contact.

Example 27: The adapter of any of examples 16-26, wherein the rotational electrical coupling is configured to conduct a cardiac electrogram signal in which His-Purkinje conduction system features can be detected during rotation of the implantable medical lead.

Example 28: A method includes receiving, by an adapter, a proximal portion of an implantable medical lead, the implantable medical lead includes an adapter body configured to receive the proximal portion of the implantable medical lead, including the lead electrical connector, and allow rotation of the proximal portion relative to the adapter body when the proximal portion is received by the adapter body; and a rotational electrical coupling within the adapter body, the rotational electrical coupling configured to electrically connect the lead electrical connector to the adapter electrical connector and includes a first conductive component configured to be electrically connected to the lead electrical connector and rotatable within the adapter body with the proximal portion of the implantable medical lead; and a second conductive component electrically connected to the first conductive component and the adapter electrical connector, the second conductive component rotationally fixed relative to the adapter body; and receiving, by a test device electrically coupled to the adapter, signals sensed via the electrode during the rotation of the implantable medical lead.

Example 29: The method of example 28, the signals sensed via the electrode during the rotation of the implantable medical lead include a cardiac electrogram signal in which His-Purkinje conduction system features can be detected.

Example 30: A method of making an adapter configured to electrically connect a test device to an implantable medical lead includes attaching a lead receptacle to a first conductive component; attaching a test device connector to a second conductive component; and forming an adapter body around the first and second conductive components, and at least portions of the lead receptacle and the test device connector, wherein the first conductive component and the lead receptacle are rotatable relative to the adapter body, and the second conductive component and the test device connector are rotationally fixed relative to the adapter body.

Example 31: The method of example 30, wherein first and second conductive components include a soft metal.

Example 32: The method of example 31, wherein first and second conductive components include graphite.

Example 33: The method of example 32, wherein the first and second conductive components consist essentially of graphite.

Example 34: The method of any of examples 30-33, further including positioning an elastically deformable element relative to the second conductive component, the elastically deformable element configured to maintain the second conductive component in abutment with the first conductive component as the first conductive component moves axially within the adapter body.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:
an implantable medical lead comprising:
    an electrode at a distal end of the implantable medical lead; and
    a lead electrical connector at a proximal portion of the implantable medical lead, the lead electrical connector electrically coupled to the electrode; and
an adapter comprising:
    an adapter body configured to receive the proximal portion of the implantable medical lead, including the lead electrical connector, and allow rotation of the proximal portion relative to the adapter body when the proximal portion is received by the adapter body;
    an adapter electrical connector configured to be electrically connected to a test device; and
    a rotational electrical coupling within the adapter body, the rotational electrical coupling configured to electrically connect the lead electrical connector to the adapter electrical connector and comprising:
        a first conductive component configured to be electrically connected to the lead electrical connector and rotatable within the adapter body with the proximal portion of the implantable medical lead, wherein the first conductive component is coaxial with a longitudinal axis of the proximal portion of the implantable medical lead, wherein the first conductive component is rotatable about the longitudinal axis with the proximal portion of the implantable medical lead when the proximal portion of the implantable medical lead is rotated, and wherein the first conductive component is further configured to move axially within the adapter body; and
        a second conductive component electrically connected to the first conductive component and the adapter electrical connector, wherein the second conductive component is coaxial with the longitudinal axis of the proximal portion of the implantable medical lead, and wherein the second conductive component is rotationally fixed relative to the adapter body when the proximal portion of the implantable medical lead is rotated.

2. The system of claim 1, wherein the second conductive component abuts the first conductive component.

3. The system of claim 2, wherein the adapter comprises an elastically deformable element within the adapter body, the elastically deformable element configured to maintain the second conductive component in abutment with the first conductive component as the first conductive component moves axially within the adapter body.

4. The system of claim 3, wherein the elastically deformable element comprises a spring.

5. The system of claim 1, wherein the first conductive component and the second conductive component comprise a soft metal.

6. The system of claim 5, wherein the first conductive component and the second conductive component comprise graphite.

7. The system of claim 1, wherein the rotational electrical coupling comprises a contact configured to receive and be electrically connected with the lead electrical connector, wherein the contact is configured to rotate within the adapter body with the proximal portion of the implantable medical lead.

8. The system of claim 7, wherein the rotational electrical coupling comprises an insulative bearing defining a channel configured to receive the proximal portion of the implantable medical lead and at least a portion of the contact, wherein the insulative bearing is configured to rotate within the adapter body with the proximal portion of the implantable medical lead.

9. The system of claim 1, wherein the electrode is extendable/retractable from the distal end of the implantable medical lead by rotation of the implantable medical lead.

10. The system of claim 1, wherein the rotational electrical coupling is configured to conduct a cardiac electrogram signal in which His-Purkinje conduction system features can be detected during rotation of the implantable medical lead.

11. An adapter configured to electrically connect a test device to an implantable medical lead, the implantable medical lead comprising an electrode at a distal end of the implantable medical lead, and a lead electrical connector at a proximal portion of the implantable medical lead, the lead electrical connector electrically coupled to the electrode, the adapter comprising:
  an adapter body configured to receive the proximal portion of the implantable medical lead, including the lead electrical connector, and allow rotation of the proximal portion relative to the adapter body when the proximal portion is received by the adapter body;
  an adapter electrical connector configured to be electrically connected to the test device; and
  a rotational electrical coupling within the adapter body, the rotational electrical coupling configured to electrically connect the lead electrical connector to the adapter electrical connector and comprising:
    a first conductive component configured to be electrically connected to the lead electrical connector and rotatable within the adapter body with the proximal portion of the implantable medical lead, wherein the first conductive component rotates about a longitudinal axis of the proximal portion of the implantable medical lead, wherein the first conductive component is rotatable about the longitudinal axis with the proximal portion of the implantable medical lead when the proximal portion of the implantable medical lead is rotated, and wherein the first conductive component is further configured to move axially within the adapter body; and
    a second conductive component electrically connected to the first conductive component and the adapter electrical connector, wherein the second conductive component is coaxial with the longitudinal axis of the proximal portion of the implantable medical lead, and wherein the second conductive component is rotationally fixed relative to the adapter body when the proximal portion of the implantable medical lead is rotated.

12. The adapter of claim 11, wherein the second conductive component abuts the first conductive component.

13. The adapter of claim 12, further comprising an elastically deformable element within the adapter body, the elastically deformable element configured to maintain the second conductive component in abutment with the first conductive component as the first conductive component moves axially within the adapter body.

14. The adapter of claim 13, wherein the elastically deformable element comprises a spring.

15. The adapter of claim 11, wherein the first conductive component and the second conductive component comprise a soft metal.

16. The adapter of claim 11, wherein the rotational electrical coupling comprises a contact configured to receive and be electrically connected with the lead electrical connector, wherein the contact is configured to rotate within the adapter body with the proximal portion of the implantable medical lead.

17. The adapter of claim 11, wherein the rotational electrical coupling comprises an insulative bearing defining a channel configured to receive the proximal portion of the implantable medical lead and at least a portion of the contact, wherein the insulative bearing is configured to rotate within the adapter body with the proximal portion of the implantable medical lead.

18. The adapter of claim 11, wherein the rotational electrical coupling is configured to conduct a cardiac electrogram signal in which His-Purkinje conduction system features can be detected during rotation of the implantable medical lead.

19. A method comprising:
  receiving, by an adapter, a proximal portion of an implantable medical lead, the implantable medical lead comprising an electrode at a distal end of the implantable medical lead, and a lead electrical connector at the proximal portion of the implantable medical lead, the lead electrical connector electrically coupled to the electrode;
  rotating, by the implantable medical lead, to advance the electrode for implantation in patient tissue, wherein the adapter comprises:
    an adapter body configured to receive the proximal portion of the implantable medical lead, including the lead electrical connector, and allow rotation of the proximal portion relative to the adapter body when the proximal portion is received by the adapter body; and
    a rotational electrical coupling within the adapter body, the rotational electrical coupling configured to electrically connect the lead electrical connector to the adapter electrical connector and comprising:
      a first conductive component configured to be electrically connected to the lead electrical connector and rotatable within the adapter body with the proximal portion of the implantable medical lead, wherein the first conductive component rotates about a longitudinal axis of the proximal portion of the implantable medical lead, wherein the first conductive component is rotatable about the longitudinal axis with the proximal portion of the implantable medical lead when the proximal portion of the implantable medical lead is rotated, and wherein the first conductive component is further configured to move axially within the adapter body; and
a second conductive component electrically connected to the first conductive component and the adapter electrical connector, wherein the second conductive component is coaxial with the longitudinal axis of the proximal portion of the implantable medical lead, and wherein the second conductive component rotationally fixed relative to the adapter body when the proximal portion of the implantable medical lead is rotated; and receiving, by a test device electrically coupled to the adapter, signals sensed via the electrode during the rotation of the implantable medical lead.

\* \* \* \* \*